United States Patent [19]

McConnell et al.

[11] Patent Number: 5,363,885

[45] Date of Patent: Nov. 15, 1994

[54] ROBOTIC SAMPLE PREPARATION SYSTEM AND METHOD

[75] Inventors: Bain C. McConnell, Winston-Salem; Robert J. Fix, Sr., Kernersville; Philip A. Deal, Winston-Salem; Timothy A. Hobbs, Greensboro; Larry S. Jordan, Lexington; Harold L. Steelman, Yadkinville, all of N.C.

[73] Assignee: R. J. Reynolds Tobacco Company, Winston-Salem, N.C.

[21] Appl. No.: 71,145

[22] Filed: Jun. 2, 1993

[51] Int. Cl.$^5$ .............................. B65B 1/04; B65B 3/04
[52] U.S. Cl. ........................................ 141/1; 141/83; 141/98; 414/225; 414/226; 422/63; 436/48; 73/864.01; 73/864.81
[58] Field of Search ................. 141/1, 5, 7, 8, 83, 141/98, 130, 192; 901/6; 414/225, 226; 422/63, 67; 436/43, 48; 73/863.01, 863.21, 864.01, 864.81, 864.82

[56] References Cited

U.S. PATENT DOCUMENTS

| | | | |
|---|---|---|---|
| 4,673,075 | 6/1987 | Ueyama et al. | 901/6 |
| 4,766,078 | 8/1988 | Gang | 436/43 |
| 4,835,711 | 5/1989 | Hutchins et al. | 364/513 |
| 4,914,966 | 4/1990 | White, Jr. et al. | 73/863.01 |
| 4,927,545 | 5/1990 | Roginski | 436/48 |
| 5,214,969 | 6/1993 | Adkins et al. | 73/866 |
| 5,229,074 | 7/1993 | Heath et al. | 436/48 |

Primary Examiner—Henry J. Recla
Assistant Examiner—Steven O. Douglas

[57] ABSTRACT

A method of and a robotic system for preparing product samples to be analyzed at a later time has a plurality of processing stations in different locations. Each station performs a different function of a process for preparing a product sample for later chemical analysis. A robot moves a first container between a container storage area and a prepared sample area for storing in a second container a product sample which has been prepared for analysis and in which the robot moves the first container from the container storage area to each of the processing stations in a predetermined sequence and then removes some of the prepared product sample from the first container and dispenses it into the second container which is located in the prepared sample area. A specific application of such a robotic sample preparation system is disclosed for use in preparing tobacco samples for analysis of nicotine and sugar content.

44 Claims, 4 Drawing Sheets

ROBOTIC SAMPLE PREPARATION SYSTEM AND METHOD

FIELD OF THE INVENTION

The present invention is directed to a method of and apparatus for the unattended preparation of samples. More particularly, the present invention is directed to a robotic sample preparation system and method for preparing samples which will be analyzed at a later time.

BACKGROUND OF THE INVENTION

A certain amount of testing usually accompanies the production of many products in order to ensure that the desired quality and other properties of those products is maintained. For example, in the tobacco and food industries, the quality of the tobacco and food prepared for sale to customers is constantly monitored in order to ensure that the products meet the specifications of the company selling those products.

One way in which products are monitored is by taking samples of the end product or the components thereof and analyzing those samples in order to determine that they meet the company's desired specifications. Often, there are many batches of such samples to be tested. Therefore, the preparation of a large number of samples which will then be tested to analyze their properties often consumes a significant amount of employee hours. In fact, the preparation of the samples themselves can oftentimes require the expenditure of a significant amount of employee hours. Therefore, it would be advantageous if the number of employee hours devoted to the preparation of samples for testing and analysis could be reduced.

One way in which to reduce the number of employee hours devoted to sample preparation is to automate the sample preparation process. In addition, the automated sample processing system can be programmed to operate at such a time that all of the prepared samples are ready for use for the analysis and monitoring procedures at a predetermined time. For example, the sample preparation system of the present invention can be operated in the evening, so that, by the next morning, the desired number of prepared samples are ready for use in the analysis and monitoring of the product.

SUMMARY OF THE INVENTION

In view of the foregoing, it should be apparent that there exists a need in the art for a system and a method for the unattended preparation of samples for later analysis in which a robotics system is utilized together with several independent processing stations in order to relieve company personnel from a manual task as well as to increase sample preparation throughput. It is, therefore, a primary object of this invention to provide a system and method for the unattended preparation of samples of products or product components which is characterized by the use of a robotic system for moving a container holding the product or product component between the various processing stations.

More particularly, it is an object of this invention to provide an unattended robotic-based sample preparation system which uses simple and reliable electronic circuitry and components and which does not require frequent maintenance or replacement of components.

More particularly, it is an object of the present invention to provide a system for the unattended preparation of samples in which an articulated robot arm and several specially designed processing stations are utilized in order to efficiently prepare samples for later chemical analysis by laboratory personnel.

Another object of the present invention is to provide a reliable system for the unattended preparation of tobacco samples for nicotine and sugar analysis in which an articulated robot arm and several specially designed processing stations are utilized, all of which is contained on a single table or bench.

Briefly described, these and other objects of the invention are accomplished by providing a single elongated table to which a track for an articulated robot arm is attached such that the robot arm may travel along substantially the length of the table in order to reach and manipulate sample preparation materials at various independently operated processing stations at different locations on the table. Such a construction allows for the flexibility to reconfigure the table for the preparation of different samples for or the use of different or additional processing stations.

Each of the individual system components is controlled in a distributed manner in order to allow for the independent operation of each processing station, thus increasing sample throughput. Although the system as described herein is designed to perform four main tasks, as will be obvious to those of ordinary skill in the art, a greater or lesser number of main tasks may be performed using the system disclosed herein.

With these and other objects, advantages and features of the invention that may become hereinafter apparent, the nature of the invention may be more clearly understood by reference to the following detailed description of the invention, the appended claims and to the several drawings attached herein.

DETAILED DESCRIPTION OF THE INVENTION

Figure 1A:
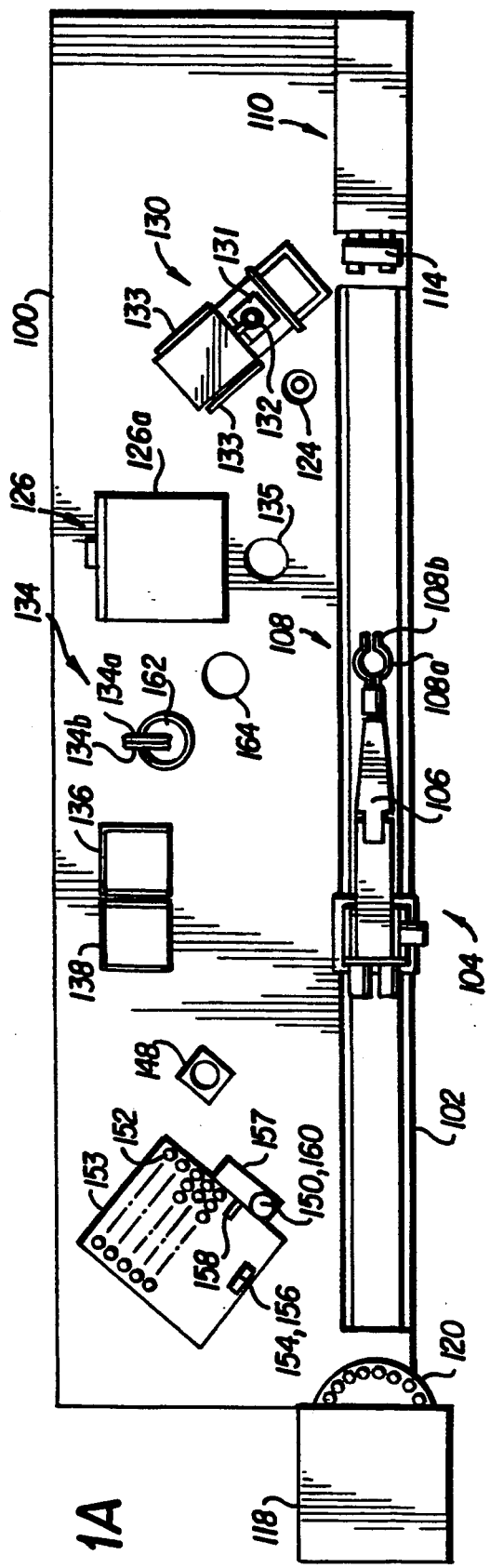
FIG. 1A is a top plan view of the system of the present invention.

Referring now in detail to the drawings wherein like parts are designated by like reference numerals throughout, there is illustrated in FIG. 1A a robot table 100 to which a robot track 102 is secured using any suitable means, such as bolts or welding. The robot 104, which may be a CRS robot available from Hudson Robotics, Inc. of Springfield, N.J., is moved along the length of the track 102 by a suitable propulsion system, such as an electric motor. The robot 104 includes an articulated robot arm 106 having a gripper 108 at one end for retrieving and manipulating sample carrying containers and other components of the system. The gripper 108 is capable of gripping with both gripping arms 108a and with gripping fingers 108b.

At one end of the table 100 is a vial rack 110 which includes a number of inclined shelves 112 which are arranged within the vial rack such that the rear portion of each of the shelves 112 is somewhat higher than the front portion of each of the shelves. Such a design allows each of the many vials 114 stored on each of the racks to roll forwardly and rest against a vial stop 116 at the front end of each shelf 112 in order to be readily available for the robot gripper 108 to pick up one at a time. The vials may preferably be a 130 ml round plastic vial which is commercially available from a number of suppliers.

At the end of the table 100 opposite to the vial rack 110 is a tray cabinet 118. The tray cabinet 118 is designed to hold a number of trays 120 containing the completed samples prepared by the system of the present invention for later retrieval by a laboratory technician for analysis.

A fiber optic retro-reflective infrared sensor 124 is located on the table 100 adjacent the robot track 102. This sensor 124 is used to detect the presence of a vial 114 in the gripper 108 of robot 104 and whether the vial is oriented properly, i.e., with the end or bottom of the vial directed downwardly, so that the vial can receive and retain a sample. Sensor 124 comprises two components, a fiber optic component which may preferably be a Model No. BT23S, available from Banner, Inc. of Minneapolis, Minn., and a detector component, which may preferably be a Model No. SN512LBFO detector also available from Banner.

A sample weighing apparatus 130 is mounted to the table 100 adjacent the vial storage rack 110 for weighing the samples to be prepared. The weighing apparatus 130 comprises an analytical scale 131 which may preferably be a Model AT200 scale available from Mettler Instrument Corporation, of Hightstown, N.J. Weighing apparatus 130 is open on both sides of scale 131 to permit the robot gripper 108 to position a vial 114 on the scale 131. Doors 133 are slidable over the openings during the weighing sequence to minimize any disturbance of the dispensed sample by air currents or the like.

Figure 1B:
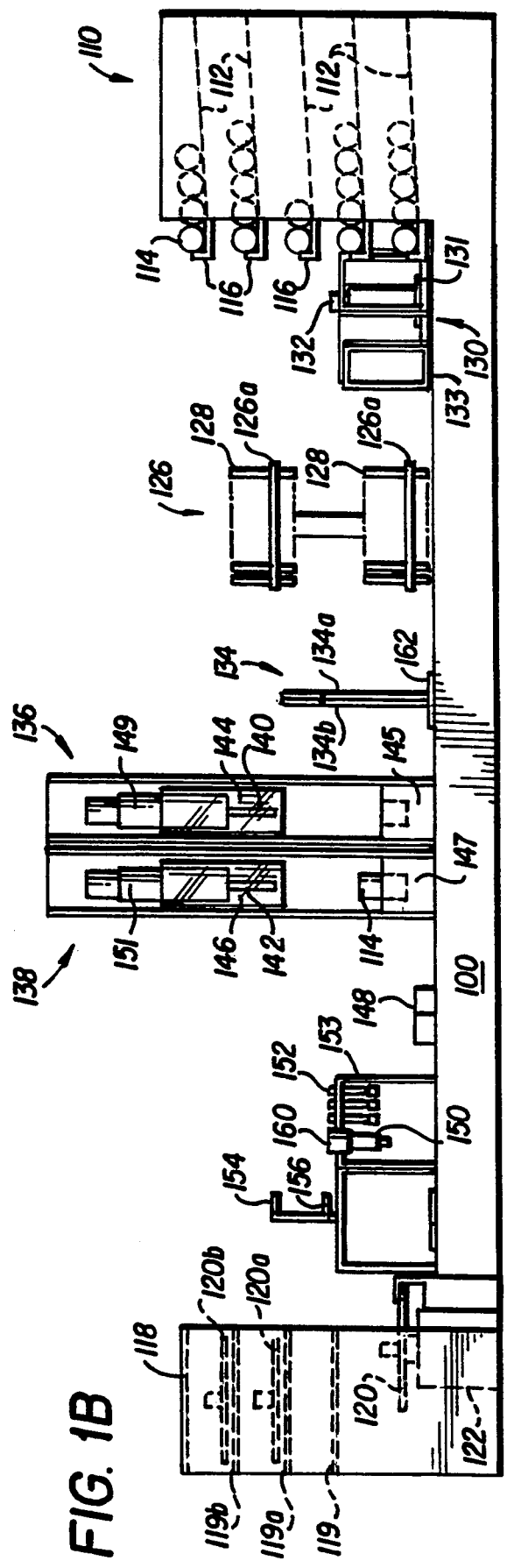
FIG. 1B is a rear elevation view of the system of the present invention with the robot and robot track omitted for clarity.

The samples to be prepared for analysis are located in a sample tube holder 126 which may be a multi-tiered tray (two trays 126a are shown in FIG. 1B). Each tray 126a holds a plurality of sample dispensing tubes 128 arranged to be picked up in a predetermined sequence by the gripping fingers 108b of robot arm 106. Each sample tube 128 contains a sample to be analyzed, e.g., ground tobacco. The tube has been previously loaded with the sample and placed in a tray by a laboratory technician. The sample dispensing tubes 128 are of a type having a dispensing opening at the bottom thereof which is closed by a valve operated by shaking or vibrating the tube with an electromagnetic tube shaker. Such dispensing tubes are available from Heirath & Andrews Corp. of Denver, Colo., under the designation SRO feeder tubes.

Located directly above the scale 131 is a tube shaker 132 for the dispensing tube 128. The tube shaker 132 may preferably be part of a Model ISOG-4107 weighing controller, also available from Heirath & Andrews. After a sample dispensing tube 128 is placed in the tube shaker 132, a controller 200 which supervises the scale 131 and shaker 132 (FIG. 2A) starts the weighing sequence by activating the tube shaker 132 and reading the scale 131 until a predetermined weight of the sample has been dispensed from the tube 128 to the vial 114. If the weight of the dispensed sample exceeds a predetermined maximum or is below a predetermined minimum the vial 114 is removed from the weighing apparatus 130 by the robot and discarded. The next sample dispensing tube in the predetermined sequence is then picked up by the robot and the weighing sequence is repeated.

The independent operation of the weighing system comprising the scale 131, the tube shaker 132 and the accompanying weighing controller 200 allows the robot 104 to perform other tasks on previously weighed samples while the weighing functions are performed as the initial step for preparing each of the samples of a batch of samples being prepared. After the correct predetermined weight of the sample, e.g., ground tobacco, has been placed in the sample vial 114, the sample tube 128 is picked up by the robot 104 and deposited in an opening 135 in the table 100 which leads via a chute to a receptacle (not shown) below the table. The sample vial 114 is then removed from the weighing system 130 by the robot 104 and moved to the next processing step located at a dispensing station 134. The dispensing station 134 includes an extraction solution dispenser 134a and 134b. Dispenser 134 comprises a pair of tubes 134a, 134b mounted side-by-side in a spigot-like arrangement. One tube 134a is connected to a vessel 302 located beneath table 100 and containing a wetting solution, e.g., a solution of methanol and acetic acid. The other tube 134b is connected to a vessel 306 containing a solution of distilled water and acetic acid. Separately controllable pumps 300, 304 are connected between the tubes 134a, 134b and their respective vessels 302, 306 for pumping the liquids therefrom to the spigot outlets of the dispenser 134 where the liquids are discharged into a vial 114 held by the gripper 108 of the robot under the spigot outlets.

The sample vial 114 containing, in the described embodiment, the ground tobacco sample and the extraction solution is then transferred by the robot 104 to one of two identical extraction stations 136, 138 which are designed to rapidly bring the nicotine and sugars in the tobacco into a solution in the sample vial 114. Once the sample vial 114 is placed in an extraction station 136 or 138, a probe controller 210, 212 (FIG. 2B) associated with the respective extraction station 136 or 138 independently operates all functioning of each respective extraction station. An ultrasonic probe 140, 142, which is enclosed in the housing of a respective extraction station 136, 138, is adapted to be lowered into contact with the solution in a vial 114. The probe may preferably be a Model No. VC-6000 ultrasonic processor probe available from Sonics & Materials, Inc. of Danbury, Conn.

At the same time the ultrasonic probe 140, 142 is lowered into contact with the solution in the vial 114, a cover 144, 146 is lowered automatically with the probe 140, 142 so as to surround the probe and the sample vial 114a in order to attenuate the sound pressure level of the extraction process to below acceptable limits. Once the nicotine and sugars are extracted from the tobacco sample, the probe and cover are raised and the vial 114 is removed from the respective extraction station 136, 138 by the robot 104 and placed in a fixture 148 mounted on the surface of the table 100. The tip of the probe 140, 142 is then lowered into a cleaning chamber 145, 147 in the bottom of a respective extraction station 136, 138 where jets of water and air are used to clean and dry the tip in order to prevent carry-over contamination to the next sample.

The next processing step involves filtering the extraction solution into a pipette for preparation of the final sample solution. After placing the sample vial 114 containing the extracted sample in the vial fixture 148, the robot 104 picks up a pipette tool 150 and places the tool over a tray 153 of plastic pipettes 152 each having a filter releasably affixed thereto. The tool 150 may preferably be a pipette tool available from Hudson Robotics, Inc. of Springfield, N.J. The pipette tool 150 has pneumatic and suction lines from 322, 324 connected thereto for operating the pipette pick-up mechanism and for drawing the solution through the filter and into the pipette. The pipette tool 150 is positioned by the robot 104 to pick up a pipette 152 and the tool with the pipette and filter are carried by the robot to a pair of optical sensors 154 and 156 which detect, respectively, the presence or absence of the pipette and the filter attached to the tip of the pipette. Each of the optical sensors 154 and 156 may be constructed from a Model No. FS2-60 sensor and FU35 optical fiber available from Keyence of Fairlawn, N.J. After the presence of both the pipette and the filter have been verified by the sensors 154 and 156, the robot 104 then lowers the pipette and filter 152 into the sample vial 114 located in the vial fixture 148. A predetermined amount of solution is withdrawn by suction from the sample vial 114 through the filter and into the pipette tip. The pipette and attached filter 152 are then moved by the robot to a filter stripping slot 158 located in tray 153 adjacent the storage location of the pipette tool 150. The robot manipulates the tool 150 so that the pipette is positioned in the slot 158 with the filter below the tray 153 so that when the tool is raised by the robot, the filter is stripped from the pipette tip. The removed filter drops through an opening 157 in table 100 and is collected in a container (not shown) beneath the table.

The pipette tip together with the filtered solution contained therein is carried to the sample tray cabinet 118 in which a circular sample tray 120 containing a number of liquid sample cups is positioned for receiving the sample solution. The trays 120, 120a, 120b which hold the liquid sample cups may preferably be Alpkem analyzer trays that are used for sample analysis on Alpkem rapid flow analyzers, such as a Model No. RFA-300, available from Alpkem Corporation, Clackamas, Oreg. The standard Alpkem analyzer trays are modified to permit them to be picked up and manipulated by the robot 104. Alpkem rapid flow analyzers are used by laboratory personnel to quantitatively measure the nicotine and sugar levels of the tobacco samples. Other types of analyzers could also be used depending on the product to be analyzed and the particular analysis sought to be made.

A tray carousel or rotating device 122 is arranged in the lower compartment of the cabinet 118 for rotating the tray 120 to present an appropriate sample cup to the pipette 152 being processed for sample storage. Each of the trays 120 may include up to 90 sample cups into each of which a pipette 152 deposits the filtered sample solution removed from each of the sample vials 114. Once all of the sample cups on the analyzer tray 120 have been prepared, the robot 104 removes the analyzer tray 120 from the carousel 122 and places it on a storage shelf 119 in the tray storage cabinet 118. The robot 104 then may select either of the other two analyzer trays 120a, 120b stored on their respective shelves 119a, 119b in the analyzer tray cabinet 118. The selected analyzer tray 120a, 120b is then placed on the carousel 122 so that each of the sample cups can be filled in turn.

After the solution in a pipette has been emptied into a sample cup, the pipette tool 150 is returned to a tool storage stand 160 attached to the pipette sample tray 153. The empty pipette 152 is ejected from the tool 150 and drops through opening 157 for collection in the same container into which the filters are discarded. The robot 104 then picks up the used sample vial 114, pours the remaining solution into a drain 162 beneath the dispenser 134 and then drops the empty sample vial 114 into a collection bin (not shown) below the table 100 through a hole 164 in the table 100.

As described above, once all of the samples for a given Alpkem analyzer tray 120 are prepared, the tray 120 is placed back into the tray cabinet 118 and the next tray 120a is retrieved and placed on the tray carousel 122. Each tray full of samples is placed back into the tray cabinet 118 where it may be later retrieved by a laboratory technician for analysis (e.g., the following morning if the samples are prepared the night before). The used sample vials 114, sample dispensing tubes 128, pipettes 152 and pipette filters may be removed from the bins where they are collected below the table and cleaned for reuse or they may be discarded.

While the foregoing system has been described for use in connection with the analysis of tobacco samples, components of the system may be modified such that the system can be used with other analytical methods, such as acid extraction and microwave digestion.

Figure 2A:
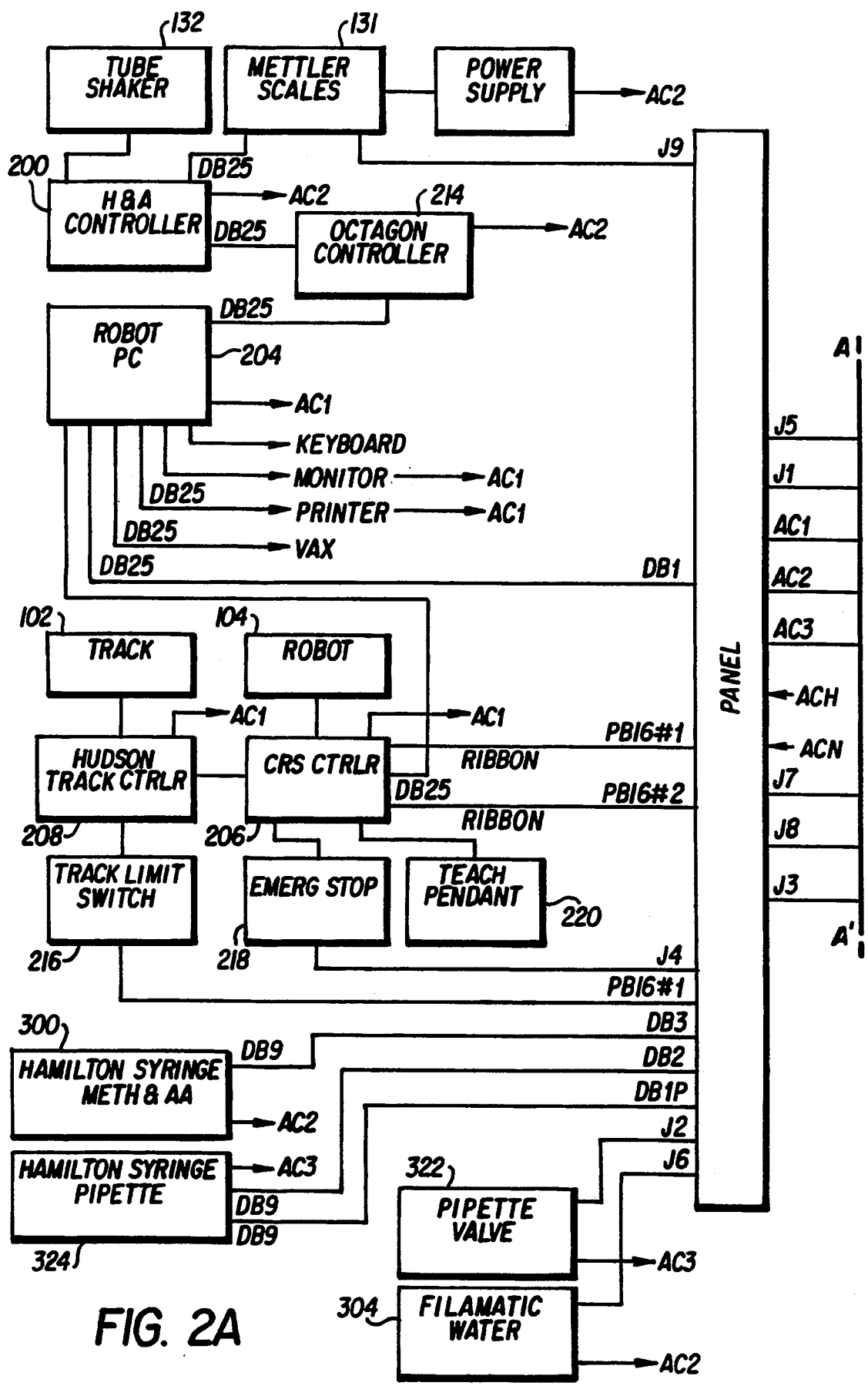
FIGS. 2A and 2B are schematic block diagrams of the electrical interconnections used with the system of the present invention.
Figure 2B:
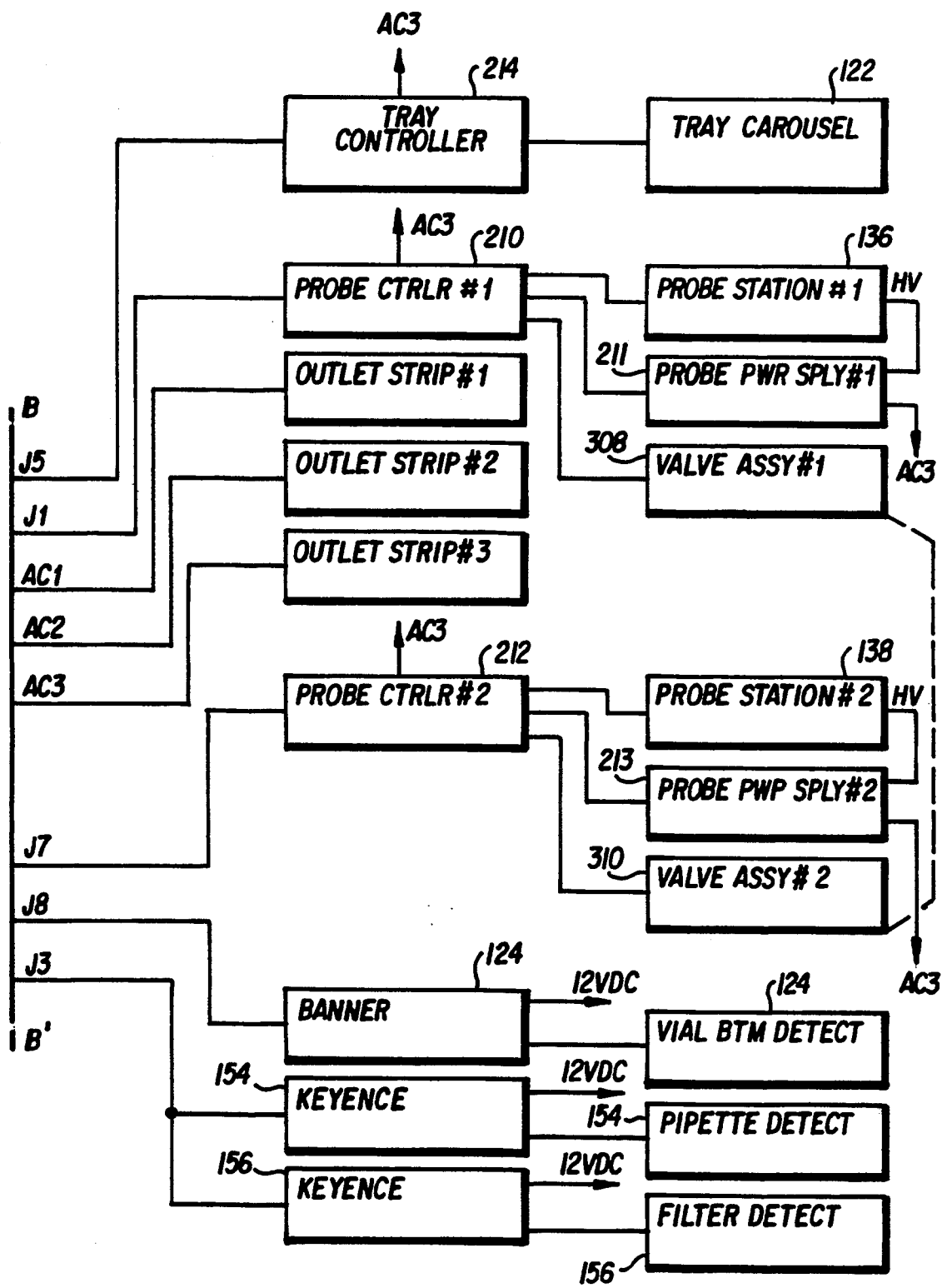
Figure 3:
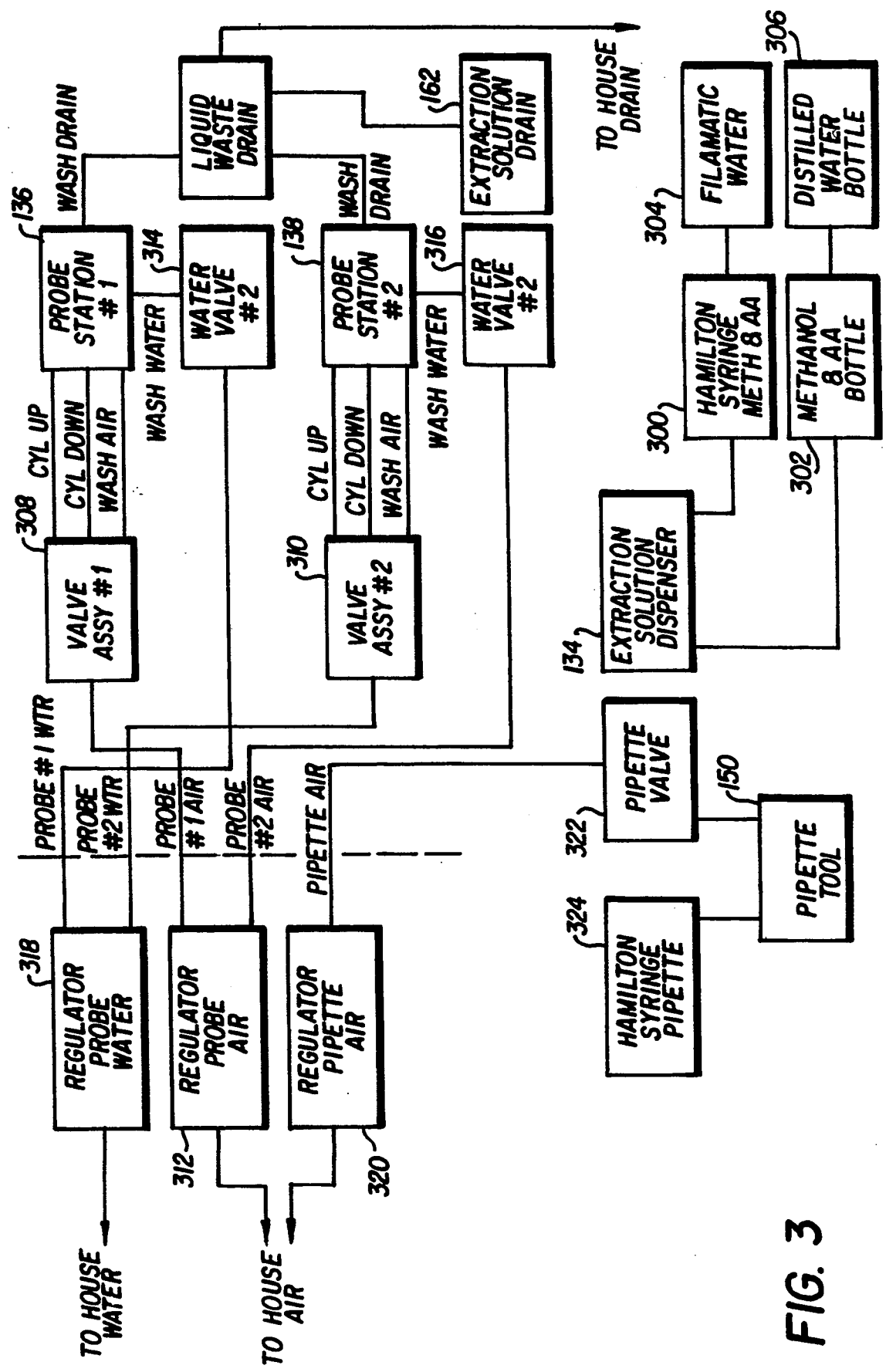
FIG. 3 is a schematic block diagram showing the fluid interconnections for the system of the present invention.

Reference is now made to FIGS. 2A, 2B and 3, as well as to FIGS. 1A and 1B, in connection with the following detailed discussion of the operation of the robotic sample preparation system of the present invention.

It should be understood that the robotic sample preparation system described herein is operated under control of a microcomputer 204, such as an IBM Model AT computer or compatible. The following is an explanation of how the personal computer is connected to and operates the inventive system.

The personal computer 204 is in two-way communication with the CRS controller 206. The computer 204 runs under control of software known as Total Control Software furnished by Hudson Robotics, Inc., of Springfield, N.J. The programs that direct the system to perform the different functions were written using that control software. The software transfers the individual commands to the CRS controller 206 and waits for a reply before proceeding to the next command. After the robot 104 has placed a sample vial onto the Mettler Scales 131 and a sample tube onto the tube shaker 132, the personal computer 204 sends a serial data command directly to the Octagon controller 214 to operate the H&A controller 200. The weight data is stored in the Octagon controller 214 until the personal computer 204 is ready to receive it. The personal computer 204 stores the weight in a file until the end of the run. At the direction of the operator, the weight file is transferred to the VAX or house computer or may be otherwise output by the personal computer 204.

After the system setup procedure is completed, the number of samples to be prepared by the system is inputted and then the robotic sample preparation system is instructed by the computer 204 to begin its operation. The balance doors 133 of the weighing apparatus 130 are then opened and the robot 104 retrieves a sample vial 114 from the vial rack 110. A determination is then made using the vial sensor 124 to insure that the robot has a vial in its grippers 108 and that the vial is properly oriented with the open end upwardly. The vial is then placed on the scale 131 and the balance doors 133 are then closed. The robot 104 then proceeds to a predetermined row and column in the sample rack 126 to select a first predetermined sample dispensing tube 128 from the many sample tubes contained in the tube sample rack 126. The robot 104 then places the selected sample dispensing tube 128 in the tube shaker 132.

The weighing apparatus 130 is then started using the controllers 214 and 200. Controller 200 initiates the weighing sequence by activating the tube shaker 132 which causes the valve at the bottom of the dispensing tube 128 to unseat and allow the ground tobacco sample to dispense in a fine stream from the dispensing opening at the bottom of the tube. The analytical scale provides a weight signal to the controller 200 deactivates the tube shaker when a predetermined weight is dispensed. The controllers 200 and 214, under supervision of the computer 204, sample the output of the scale 131.

If the fill is within predetermined limits the sample weight in the vial 114 is written to a file in computer 204 and the sample preparation sequence proceeds. Robot 104 removes the sample dispensing tube 128 from the tube shaker 132 and deposits it in opening 135 in the table. Balance doors 133 are then opened and the robot 104 removes the vial 114 with the predetermined weight of sample, checks vial orientation and the presence of a sample at the sensor 124 and carries the vial to the liquid dispensing station 121.

At the dispensing station 121 the robot 104 holds the vial 114 beneath the dispenser 134 and an initial solution of methanol and acetic acid is then pumped out of the methanol and acetic acid solution bottle 302 by a methanol and acetic alcohol syringe 300, through the dispenser tube 134b and into the sample vial 114 held in place by the robot 104. The gripper 108 then tilts the vial from side-to-side to thoroughly wet the sample and form a slurry-like suspension. An additional solution of acetic acid and distilled water is then pumped through the dispenser tube 134a by a pump 304 and into the vial with the wetted sample.

The sample vial 114 containing the extraction solution is then transferred to one of the extraction stations 136, 138 and placed in a selected extraction station by the robot 104. The extraction stations 136, 138 are under control of a respective probe controller 210, 212 which are in turn controlled by computer 204. Controllers 210, 212 control the valve assemblies 308, 310 for the air used in the cleaning chambers 145, 147 and in the air cylinders 149, 151 for raising and lowering the probes 140, 142 and the probe covers 144, 146, the power to the ultrasonic probes 140, 142 and the water valves 314, 316 for the water used to clean the probes in the respective cleaning chambers 145, 147.

Flow of air and water to the valve assemblies 308, 310 and water valves 314, 316 is regulated by a pair of air and water regulators 312, 318. Assuming a vial 114 is located in extraction station 138, controller 212 initiates the extraction sequence for this station after the robot 104 places a vial 114 into a receptacle in the extraction station 138. First, the probe cover 146 is lowered into position over the vial. The ultrasonic probe 142 is then lowered into the solution in vial 114 and power is applied for a predetermined time to probe 142 from the power supply 213. The ultrasonic energy generated by the probe 142 rapidly solubilizes the nicotine and sugars in the tobacco sample in the vial. When the power is terminated to the probe 142, it is raised along with the probe cover 146 to clear the vial.

The controller 212 then signals that the vial is ready for pick up by the robot 104 which picks up the vial and places it in fixture 148. Controller 212 then functions to operate the valve assembly 310 to lower the probe 142 and its associated cover 146 such that the probe 142 is positioned in the cleaning chamber 147. Controller 212 then activates valve assembly 310 and water valve 316 to clean and dry the probe 142. A preferred cleaning and drying sequence is as follows: The water valve 316 is opened for three seconds, then power is applied to the probe 142 by power supply 213 for two seconds and then valve assembly 310 is opened for two seconds to dry the probe 142. The probe 142 is then raised to its top most position and the probe controller 212 then signals the microcomputer 204 that the probe station 138 is ready to receive another sample vial 114. The operation of extraction station 136, its controller 210, power supply 211, cleaning chamber 145, valve assembly 308 and water valve 314 are identical to that described above for extraction station 138.

In the final sample preparation sequence, the robot 104 picks up the pipette tool 150 from its holder 160 on tray 153 and then proceeds to a preselected row and column of tray 153 in which a pipette with filter 152 is located. The robot 104 moves the pipette tool 150 to a position over the pipette where the tool picks up the selected pipette 152 with attached filter. After checking for the presence of a pipette and filter with sensors 154, 156, the pipette 152 and filter are placed in the solution in vial 114 located in fixture 148. If no pipette and filter are detected by sensors 154, 156, the robot is directed to return tool 150 to tray 153 for another pipette pick up. If a pipette is detected by sensor 154, but no filter is detected by sensor 156, the robot 104 is directed to discard the pipette in the opening 157 and to pick up another pipette 152 and filter from tray 153.

Using an automatic syringe 324, a sample is drawn by suction from the sample vial 114. The robot 104 then moves the pipette and filter to the filter stripping device 158 where the filter is stripped from the pipette tip and discarded into opening 157. The robot then moves the pipette to a predetermined sample cup of the analyzer sample tray 120 and dispenses the sample solution into the sample cup. The pipette is then discarded into opening 157 and the pipette tool 150 is returned to the tool stand 160.

After the predetermined sample cup of the analyzer sample tray 120 is filled with the sample solution, the carousel 122, under control of the tray controller 214, indexes the tray by one position and then produces a ready signal signaling that it is ready to receive another sample. After each of the sample cups has been filled, the tray controller 214 signals the microcomputer 204 that the tray 120 is ready for pick up. The robot 104 then removes tray 120 from the carousel 122 and places it on its shelf 119 in the tray cabinet 118. Thereafter, the robot is directed to pick up another tray 120a and locate it on the tray carousel 122 for receiving another batch of samples.

Although only a very brief description of the robot track 102 has been given herein, it will be obvious to those of ordinary skill in the art that such a track 102 will usually include track limit switches 216 connected to track controller 208, as well as an emergency stop switch 218 connected to the robot controller 208. A teach pendant 220 is also connected to the robot controller 206 and is used in programming the positioning of the robot 104, robot arm 106 and gripper 108 with the robot microcomputer 204.

Although only a preferred embodiment is specifically illustrated and described herein, it will be appreciated that many modifications and variations of the present invention are possible in light of the above teachings and within the preview of the appended claims without departing from the spirit and intended scope of the invention.

What is claimed is:

1. A method for operating a robotic sample preparation system for preparing product samples to be analyzed at a later time, comprising the steps of:
    filling an empty sample solution container with a predetermined amount of product sample to be analyzed;
    moving said sample solution container containing said product sample to a dispensing station using said robotic system;
    dispensing at said dispensing station an extraction fluid into said sample solution container containing said product sample to form a sample solution in said sample solution container;
    moving said sample solution container containing said sample solution to an extraction station using said robotic system;
    extracting components of said product sample into said sample solution so as to form an extracted solution in said sample solution container;
    removing and filtering a predetermined amount of said extracted solution from said sample solution container using said robotic system and an extracted solution container; and
    using said robotic system to dispense said predetermined amount of extracted solution from said extracted solution container into one of a plurality of sample preparation cups which are included in a sample container for later analysis of said extracted solution.

2. The method of claim 1, further including the step of determining that said empty sample solution container is oriented in a proper direction prior to receiving said product sample.

3. The method of claim 1, wherein said filling, moving, dispensing, extracting, removing and filling and using steps are all controlled independently of each other under direction of a digital data processor.

4. The method of claim 1, wherein said sample container comprises a first rotatable tray which includes a plurality of sample preparation cups each for receiving a predetermined amount of said extracted solution.

5. The method of claim 4, further including the step of rotating said first rotatable tray after each of said plurality of sample preparation cups is filled until each of said plurality of sample preparation cups is filled with a different extracted solution sample.

6. The method of claim 5, further including the steps of removing said first rotatable tray containing a plurality of filled sample preparation cups and replacing said first rotatable tray with a second rotatable tray, said second rotatable tray having a like plurality of sample preparation cups.

7. The method of claim 1, wherein said removing and filtering step comprises detecting the presence of a filter device attached to said extracted solution container.

8. The method of claim 7, wherein said removing and filtering step comprises the step of removing said filter device from said extracted solution container prior to using said robotic system to dispense said extracted solution from said extracted solution container.

9. The method of claim 1, wherein said extracting step comprises subjecting said sample solution to ultrasonic energy in order to extract components of said product sample into solution.

10. A method for operating a robotic sample preparation system for preparing product samples to be analyzed at a later time, comprising the steps of:
    filling an empty sample solution container with a predetermined amount of product sample to be analyzed;
    moving said sample solution container containing said product sample to a dispensing station using said robotic system;
    dispensing at said dispensing station an extraction fluid into said sample solution container containing said product sample to form a sample solution in said sample solution container;
    moving said sample solution container containing said sample solution to an extraction station using said robotic system;
    extracting components of said product sample into said sample solution so as to form an extracted solution in said sample solution container, wherein said extracting step comprises subjecting said sample solution to ultrasonic energy in order to extract components of said product sample into solution;
    removing and filtering a predetermined amount of said extracted solution from said sample solution container using said robotic system and an extracted solution container; and
    using said robotic system to dispense said predetermined amount of extracted solution from said extracted solution container into a sample container for later analysis of said extracted solution.

11. The method of claim 10, wherein said removing and filtering step comprises detecting the presence of a filter device attached to said extracted solution container.

12. The method of claim 11, wherein said removing and filtering step comprises the step of removing said filter device from said extracted solution container prior to using said robotic system to dispense said extracted solution from said extracted solution container.

13. The method of claim 10, wherein said sample container comprises a first rotatable tray which includes a plurality of sample preparation cups each for receiving a predetermined amount of said extracted solution.

14. The method of claim 13, further including the step of rotating said first rotatable tray after each of said plurality of sample preparation cups is filled until each of said plurality of sample preparation cups is filled with a different extracted solution sample.

15. The method of claim 14, further including the steps of removing said first rotatable tray containing a plurality of filled sample preparation cups and replacing said first rotatable tray with a second rotatable tray, said second rotatable tray having a like plurality of sample preparation cups.

16. The method of claim 10, further including the step of determining that said empty sample solution container is oriented in a proper direction prior to receiving said product sample.

17. The method of claim 10, wherein said filling, moving, dispensing, extracting, removing and filling and using steps are all controlled independently of each other under direction of a digital data processor.

18. A method of operating a robotic sample preparation system for preparing samples to be analyzed at a later time, comprising:
   providing a plurality of processing stations in different locations each for performing a different function for a process of preparing a product sample for later chemical analysis;
   using a robotic system for moving a first container between a container storage area and a prepared sample area for storing a product sample which has been prepared for analysis, said robotic system moving said first container from said container storage area to each of said processing stations in a predetermined sequence;
   determining whether said first container is oriented in a proper direction for receiving a predetermined amount of said product sample; and
   said robotic system further removing some of said prepared product sample from said first container and dispensing said removed prepared product sample into one of a plurality of second containers in said prepared sample area.

19. The method of claim 18, wherein each of said plurality of processing stations is controlled independently of each other under direction of a digital data processor.

20. The method of claim 18, wherein said prepared sample area comprises, a sample tray cabinet which includes a plurality of sample trays each having a plurality of second containers for receiving a predetermined amount of said prepared product sample.

21. The method of claim 20, further including the step of rotating a first one of said plurality of sample trays so as to fill each of said plurality of second containers with a predetermined amount of said prepared product sample.

22. The method of claim 21, further including the step of rotating said first one of said plurality of sample trays after each one of said plurality of second containers is filled until each one of said plurality of second containers is filled with a different prepared product sample.

23. The method of claim 22, further including the step of removing said first one of said plurality of sample trays containing a plurality of filled second containers and replacing said removed first one of said plurality of sample trays with a second one of said plurality of sample trays.

24. The method of claim 18, wherein said step of removing some of said prepared product comprises detecting the presence of a filter device attached to a device for dispensing some of said prepared product sample into said second container.

25. The method of claim 24, wherein said step of removing some of said prepared product sample comprises the step of removing said filter device from said device for dispensing prior to said step of dispensing said prepared product sample into said second container.

26. The method of claim 18, further including the step of extracting components of said product sample into solution by dispensing an extraction solution into said first container and then subjecting said product sample and extraction solution to ultrasonic energy.

27. A robotic sample preparation system for preparing product samples to be analyzed at a later time, comprising:
   a storage system for holding a plurality of sample solution containers;
   a weighing system for weighing a quantity of product sample dispensed into each of said plurality of sample solution containers;
   an extraction solution dispensing system for dispensing a predetermined amount of extraction solution into each of said plurality of sample solution containers after said quantity of product sample has been dispensed into each of said containers;
   an extraction system for extracting components of said product sample into solution in one of said plurality of sample solution containers to form an extracted solution;
   a filtering system for filtering a predetermined portion of said extracted solution;
   a second storage system comprising a plurality of containers for storing said predetermined portion of said extracted solution; and
   a robotic system for removing one of said plurality of sample solution containers from said storage system and for moving the removed sample solution container between said weighing, extraction solution dispensing, extraction, and filtering systems as well as for dispensing filtered extracted solution into said second storage system.

28. The system of claim 22, further including a sensing device for determining that each one of said plurality of sample solution containers is oriented in a proper direction prior to receiving said quantity of product sample.

29. The system of claim 27, wherein each of said weighing, extraction solution dispensing, extraction, filtering and storage systems are connected to a digital data processor for controlling each of said systems independently of the others 30. The system of claim 27, wherein said second storage system comprises a first rotatable tray connected to a rotating device, said first rotatable tray including a plurality of sample preparation containers, each for receiving a predetermined amount of the filtered extracted solution.

31. The system of claim 30, wherein said second storage system further comprises at least a second rotatable tray which may be connected to said rotating device in place of said first rotatable tray, said second rotatable tray including a plurality of sample preparation containers, each for receiving a predetermined amount of said filtered extracted solution.

32. The system of claim 27, wherein said extraction system comprises at least one ultrasonic probe for applying ultrasonic energy to said product sample and extraction solution.

33. A method of operating a robotic sample preparation system for preparing samples to be analyzed at a later time, comprising:
   providing a plurality of processing stations in different locations each for performing a different function for a process of preparing a product sample for later chemical analysis;
   using a robotic system for moving a first container between a container storage area and a prepared sample area for storing a product sample which has been prepared for analysis, said robotic system moving said first container from said container storage area to each of said processing stations in a predetermined sequence;

determining whether said first container is oriented in a proper direction for receiving a predetermined amount of said product sample;

extracting components of said product sample into solution by dispensing an extraction solution into said first container and then subjecting said product sample and extraction solution to ultrasonic energy; and said robotic system further removing some of said prepared product sample from said first container and dispensing said removed prepared product sample into a second container in said prepared sample area.

34. The method of claim 33, further including the step of determining whether said first container is oriented in a proper direction for receiving a predetermined amount of said product sample.

35. The method of claim 33, wherein each of said plurality of processing stations is controlled independently of each another under direction of a digital data processor.

36. The method of claim 33, wherein said prepared sample area comprises, a sample tray cabinet which includes a plurality of sample trays each having a plurality of second containers for receiving a predetermined amount of said prepared product sample.

37. The method of claim 36, further including the step of rotating a first one of said plurality of sample trays so as to fill each of said plurality of second containers with a predetermined amount of said prepared product sample.

38. The method of claim 37, further including the step of rotating said first one of said plurality of sample trays after each one of said plurality of second containers is filled until each one of said plurality of second containers is filled with a different prepared product sample.

39. The method of claim 38, further including the step of removing said first one of said plurality of sample trays containing a plurality of filled second containers and replacing said removed first one of said plurality of sample trays with a second one of said plurality of sample trays.

40. The method of claim 33, wherein said step of removing some of said prepared product comprises detecting the presence of a filter device attached to a device for dispensing some of said prepared product sample into said second container.

41. The method of claim 40, wherein said step of removing some of said prepared product sample comprises the step of removing said filter device from said device for dispensing prior to said step of dispensing said prepared product sample into said second container.

42. A robotic sample preparation system for preparing product samples to be analyzed at a later time, comprising:

a storage system for holding a plurality of sample solution containers;

a weighing system for weighing a quantity of product sample dispensed into each of said plurality of sample solution containers;

an extraction solution dispensing system for dispensing a predetermined amount of extraction solution into each of said plurality of sample solution containers after said quantity of product sample has been dispensed into each of said containers;

an extraction system for extracting components of said product sample into solution in one of said plurality of sample solution containers to form an extracted solution; said extraction system comprising at least one ultrasonic probe for applying ultrasonic energy to said product sample and extraction solution;

a filtering system for filtering a predetermined portion of said extracted solution;

a second storage system for storing said predetermined portion of said extracted solution; and a robotic system for removing one of said plurality of sample solution containers from said storage system and for moving the removed sample solution container between said weighing, extraction solution dispensing, extraction, and filtering systems as well as for dispensing filtered extracted solution into said second storage system.

43. The system of claim 42, wherein said storage system comprises a first rotatable tray connected to a rotating device, said first rotatable tray including a plurality of sample preparation containers, each for receiving a predetermined amount of the filtered extracted solution.

44. The system of claim 43, wherein said second storage system further comprises at least a second rotatable tray which may be connected to said rotating device in place of said first rotatable tray, said second rotatable tray including a plurality of sample preparation containers, each for receiving a predetermined amount of said filtered extracted solution.

* * * * *

UNITED STATES PATENT AND TRADEMARK OFFICE
CERTIFICATE OF CORRECTION

PATENT NO. : 5,363,885
DATED : November 15, 1994
INVENTOR(S) : Bain C. McConnell, et al.

It is certified that error appears in the above-indentified patent and that said Letters Patent is hereby corrected as shown below:

Col. 12, Claim 28, first line – "22" -- change to 27 --.

Signed and Sealed this

First Day of April, 1997

Attest:

Attesting Officer

BRUCE LEHMAN

Commissioner of Patents and Trademarks